(12) United States Patent
Stern

(10) Patent No.: US 9,271,861 B1
(45) Date of Patent: Mar. 1, 2016

(54) DEVICE AND METHOD OF TREATING A NAIL CONDITION

(71) Applicant: Alan M. Stern, Jericho, NY (US)

(72) Inventor: Alan M. Stern, Jericho, NY (US)

(*) Notice: Subject to any disclaimer, the term of this patent is extended or adjusted under 35 U.S.C. 154(b) by 0 days.

(21) Appl. No.: 14/729,967

(22) Filed: Jun. 3, 2015

(51) Int. Cl.
*A61F 5/11* (2006.01)

(52) U.S. Cl.
CPC .......................................... *A61F 5/11* (2013.01)

(58) Field of Classification Search
CPC combination set(s) only.
See application file for complete search history.

(56) References Cited

U.S. PATENT DOCUMENTS

| | | | |
|---|---|---|---|
| 2,902,146 A | 9/1959 | Doherty | |
| 5,078,968 A | 1/1992 | Nason | |
| 5,181,914 A | 1/1993 | Zook | |
| 5,869,003 A | 2/1999 | Nason | |
| 6,189,539 B1 | 2/2001 | Mitchell | |
| 6,248,294 B1 | 6/2001 | Nason | |
| 6,503,013 B2 | 1/2003 | Strauss | |
| 6,536,975 B1 * | 3/2003 | Tufts | A45D 34/04 401/133 |
| 7,637,679 B2 | 12/2009 | May et al. | |
| 8,702,636 B2 | 4/2014 | Stern | |
| 2007/0287945 A1 | 12/2007 | Cha | |
| 2012/0310231 A1 | 12/2012 | McErlean et al. | |

* cited by examiner

*Primary Examiner* — Ophelia A Hawthorne
(74) *Attorney, Agent, or Firm* — Gottlieb, Rackman & Reisman, PC

(57) ABSTRACT

A device and method for treating an ingrown nail condition is provided. The device prevents a solution that is applied during a procedure from coming into contact with the surrounding skin and nail bed. The device includes a plastic tube that has a flap located at one end. An applicator is inserted through the tube to ensure direct application of a phenol or similar solution onto only a nail matrix. As a result, the phenol or similar solution is prevented from coming into contact with the surrounding skin and nail bed, thereby reducing post-operative healing time, post-operative infection and post-operative pain.

18 Claims, 3 Drawing Sheets

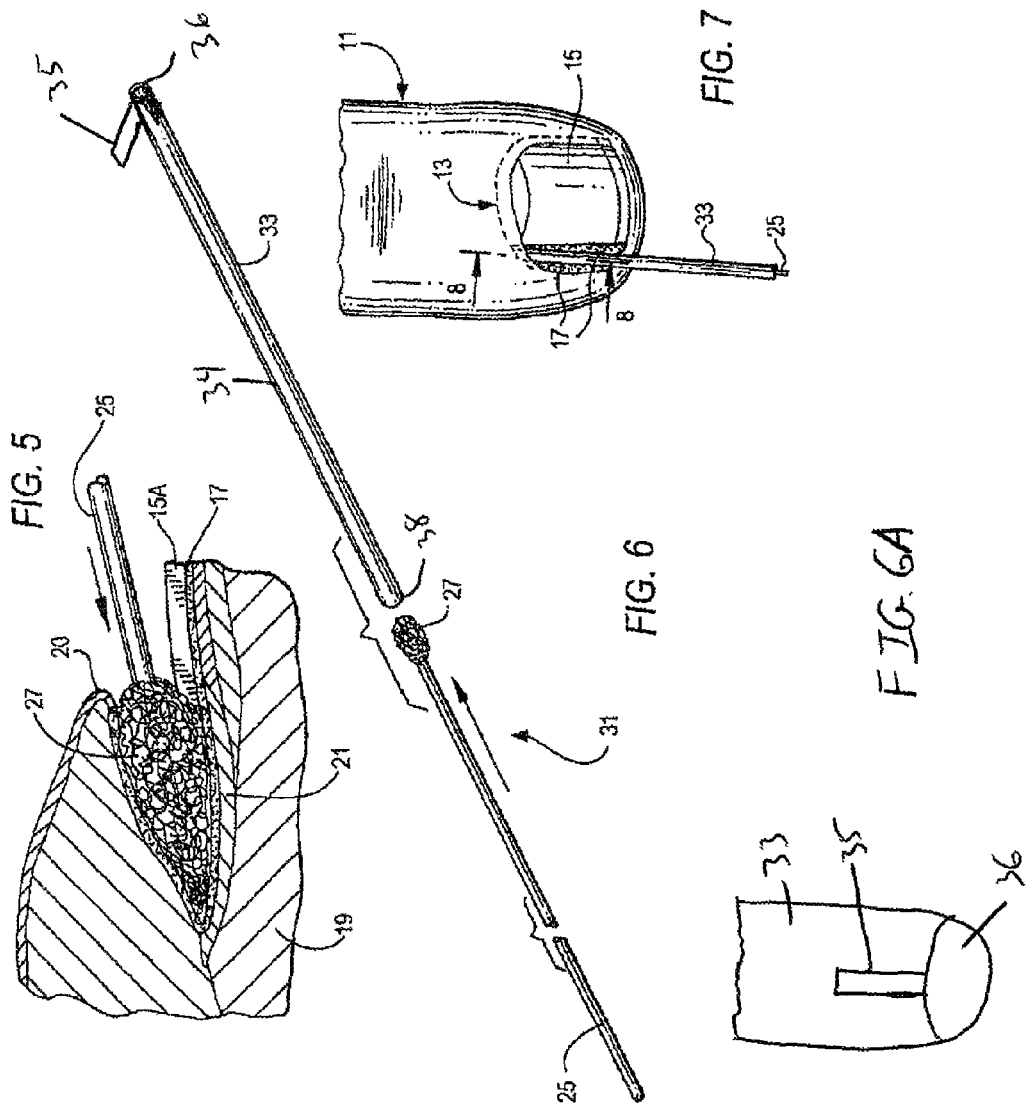

DEVICE AND METHOD OF TREATING A NAIL CONDITION

FIELD OF THE INVENTION

The present invention relates to a device and method of treating a nail condition, and more particularly, to an applicator system and method of using the applicator system to treat an ingrown nail condition.

BACKGROUND OF THE INVENTION

An ingrown toenail is a common form of nail disease. It is an often painful condition in which the nail grows so that it cuts into the side of a nail fold. While ingrown nails can occur in both the nails of the hand and feet, they occur most frequently with the toenails. A true ingrown toenail is caused by the actual penetration of the flesh by a sliver of a nail.

The most common cause of an ingrown toenail is cutting one's toenail too short. Other causes of an ingrown toenail can be from wearing socks and shoes that are tight or short, a fungal infection and trauma, for example from stubbing your toe or having an object fall on an individual's toenail.

Symptoms of an ingrown nail can include, without limitation, pain, redness and swelling of the toe or infection. Pain can occur along the margins of the nail with the pain worsening when wearing tight footwear and sensitivity to pressure of any kind. Bumping an affected toe can produce sharp, even excruciating pain as the tissue is punctured further by the nail. By the very nature of the condition, ingrown nails become easily infected unless special care is taken to treat the condition early on and keep the area clean. Signs of infection include redness and swelling of the area around the nail, drainage of fluid and watery discharge tinged with blood or purulent discharge.

Ingrown toenails that are left untreated can eventually lead to osteomyelitis, which is an infection in the bone. This serious infection can be especially severe for individuals with diabetes or circulatory problems in their lower extremities.

Treatment of ingrown toenails depends upon the severity of the condition. A podiatrist may recommend a simple treatment such as soaking one's foot in Epsom salts or in an antibacterial solution. Treatment may also include trimming of the ingrown toenail. However, in many instances, these are only temporary solutions as ingrown toenails tend to reoccur and become chronic.

A more permanent treatment option is to perform what is known as a P & A (phenol and alcohol) or partial matrixectomy procedure. This procedure eliminates the nail matrix, which is located behind and underneath the cuticle where the ingrown toenail grows to ensure that the nail does not grow back where the matrix has been cauterized/ablated so the chances of further ingrowths are substantially reduced. Occasionally, the ingrown nail can reoccur which would then require the procedure to be performed again.

Typically, in a P & A procedure, a podiatrist first injects a local anesthetic into an appendage (e.g., finger, toe) to numb it. The podiatrist next applies a tourniquet to prevent bleeding while the procedure is being performed. The ingrown nail is then removed. The amount of nail that is removed is approximately two to three millimeters or slightly more. In order to remove the nail matrix, a strong acid such as phenol is used in the procedure.

Specifically, in a P & A procedure a cotton tip applicator is saturated with phenol, which is a very strong acid solution. The applicator is then inserted under the skin until it comes into contact with the nail matrix. The applicator is then continuously rotated on the matrix for approximately thirty seconds. The treatment typically comprises a total of three applications for a combined total of approximately ninety seconds. This procedure destroys the matrix area in order to permanently and selectively ablate the matrix that is manufacturing the ingrown portion of the nail (i.e., the nail margin). The surgical site is then irrigated with alcohol to flush out the remaining phenol. A topical antibacterial ointment or cream may thereafter be applied followed by the application of a dry sterile dressing. The tourniquet is then removed.

However, in the above-described surgical procedure, a phenol solution usually comes into contact with the skin and nail bed, which regularly causes burning and damage to these soft tissue structures, producing post-operative pain, prolonging the healing at the surgical site and, in some instances, leading to post-operative infection. Eliminating and/or reducing the contact of phenol with the skin and/or nail bed would aid in reducing burning, post-operative pain and the time required for healing of the surgical site.

SUMMARY OF THE INVENTION

Accordingly, it is an object of the invention to provide an improved method and system for treating in-grown nail conditions.

Additionally, it is an object of the invention to provide a device for preventing the phenol solution that is applied during a P & A procedure from inadvertently coming into contact with surrounding soft tissue structures.

Still a further object of the invention is to provide a method for treating ingrown nails which promotes healing and reduces post-surgical complications.

The present invention is directed to a device and method for treating an ingrown nail condition where the device prevents a phenol or a similar solution from contacting surrounding skin (e.g., nail fold) and the nail bed of the ingrown nail. To prevent a phenol or similar solution from contacting the surrounding skin and nail bed of an ingrown nail, in an embodiment, the device includes a tube that has a body with a first end and a second end and a specially shaped flap, or protrusion, located near one end of the tube.

In an embodiment, the tube is comprised of plastic and can be substantially cylindrical. In an embodiment, the flap is substantially rectangular. In an embodiment, the flap is formed integral with and extends from the body of the tube near the first end of the tube at a first angle toward the second end of the tube. In an embodiment, the flap is formed integral with and extends from the body of the tube near the first end of the tube at a first angle toward the first end of the tube. In an embodiment, the flap can be of various widths and lengths, in order to allow a portion of flap to protrude from the surgical area. The flap does not require a spring or a hinge and does not rotate.

In an embodiment, the flap is flexible and resilient to provide further protection for the surrounding skin. In an embodiment, the flap and tube are both flexible. As such, upon an application of downward pressure on the flap, the flap is adaptable to bend toward the second end or the first end of the tube and contact the body of the tube and the tube is adaptable to be compressed at an end of the tube adjacent the flap as well. As a result, the flap and tube can be manipulated to be arranged underneath the cuticle. Once under the skin, the release of downward pressure on the tube and the flap allows the flap and tube to return toward an initial, non-flattened state under the skin, positioning the skin further away from the application site. By lifting the skin using primarily the flap, it is less likely that phenol or a similar solution will come into contact with the skin at the point of application, thus reducing any damage or burning of the skin.

In an embodiment, once the tube is arranged in position under the skin, an applicator that has phenol or a similar solution applied to a tip thereof is then inserted into the second end of the tube and pushed through the first end of the tube to ensure a direct application of a phenol or similar solution onto only the nail matrix. The tube and flap prevent the phenol or similar solution from contacting the surrounding skin and nail bed by forming an enclosed channel that extends from the tip of the nail to the nail matrix and by raising the skin in the region of the procedure. As a result of the phenol solution being prevented from coming into contact with the skin and nail bed, post-operative healing time, post-operative infection and post-operative pain is reduced.

To remove the tube from the surgical site, the applicator that has phenol or a similar solution applied to a tip is first removed then downward pressure is applied to the exposed portion of the flap and the tube is thereby easily withdrawn from beneath the skin with only a small amount of any residual phenol or a similar solution remaining at the tip of the tube. Accordingly, by reducing the likelihood that phenol or a similar solution comes into contact with skin at the point of application or withdrawal, there is a significant reduction of post-operative healing time, post-operative infection, and post-operative pain.

BRIEF DESCRIPTION OF THE DRAWINGS

Reference is made to the following drawings in which:

FIG. 5 is a cross-sectional view taken along line 5-5 of FIG. 4;

FIG. 6 is an exploded perspective view of an embodiment of a tube that includes a flap along with the cotton tip applicator that is insertable therein;

FIG. 6A is a partial top view of the tube of FIG. 6 showing the flap attached thereto;

FIG. 7 is a top plan view of the tube of FIG. 6 with the cotton tip applicator inserted therein and placed under the skin of the toenail so that there is direct application of the cotton tip onto only the nail matrix;

DETAILED DESCRIPTION OF EMBODIMENTS OF THE INVENTION

Figure 1:
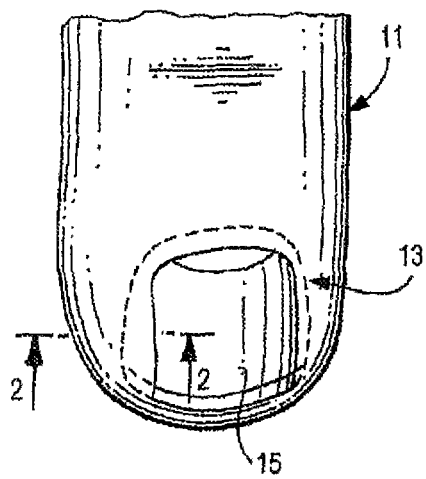
FIG. 1 is a top plan view showing an ingrown toenail.
Figure 3:
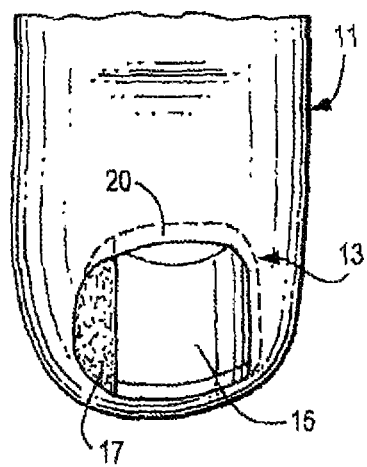
FIG. 3 is a top partial cut-away plan view of FIG. 1 depicting both the nail plate and the nail bed.
Figure 2:
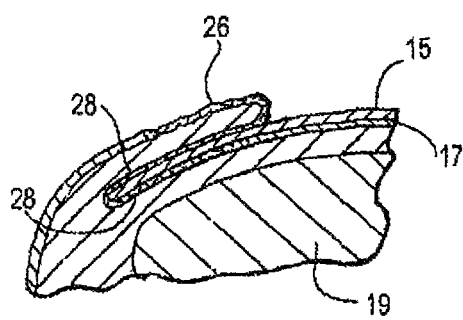
FIG. 2 is a cross-sectional view taken along line 2-2 of FIG. 1.

Referring to FIGS. 1-5, a human toe 11 is shown. The toe 11 leads to a distal end that defines a toenail 13. The toenail 13 includes a nail plate 15, which is the actual nail member. The nail plate 15 rests upon a nail bed 17, which is the skin beneath nail plate 15. The nail plate 15 is attached to a nail matrix 21, which extends beneath the nail root. Below the nail matrix 21 is a bone 19 of the toe 11 (see FIG. 5). The toe 11 also includes a nail cuticle or nail fold 20, which is a thickened layer of skin surrounding the nail plate 15.

Figure 4:
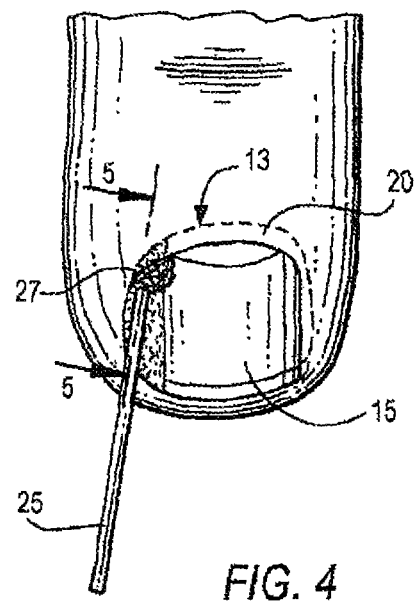
FIG. 4 is a top plan view illustrating a known placement of a cotton tip applicator under the cuticle and skin of the toenail.
Figure 8:
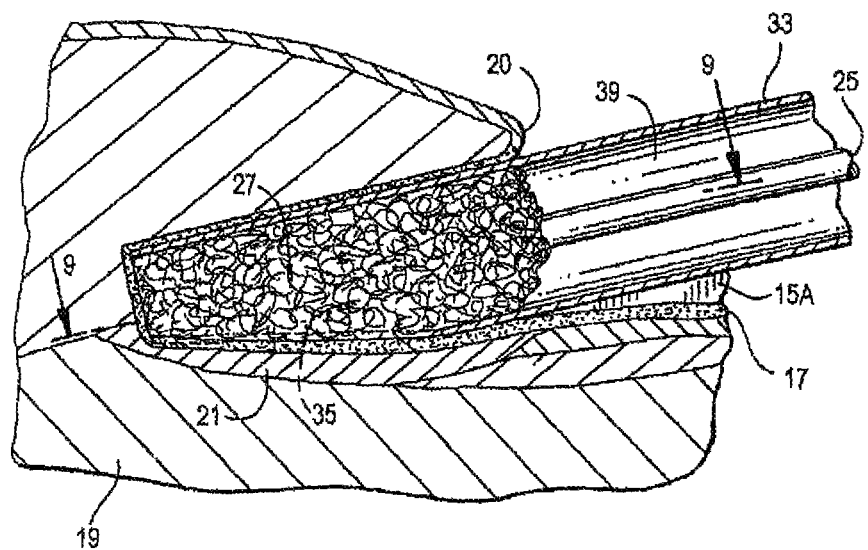
FIG. 8 is a cross-sectional view taken along line 8-8 of FIG. 7.
Figure 9:
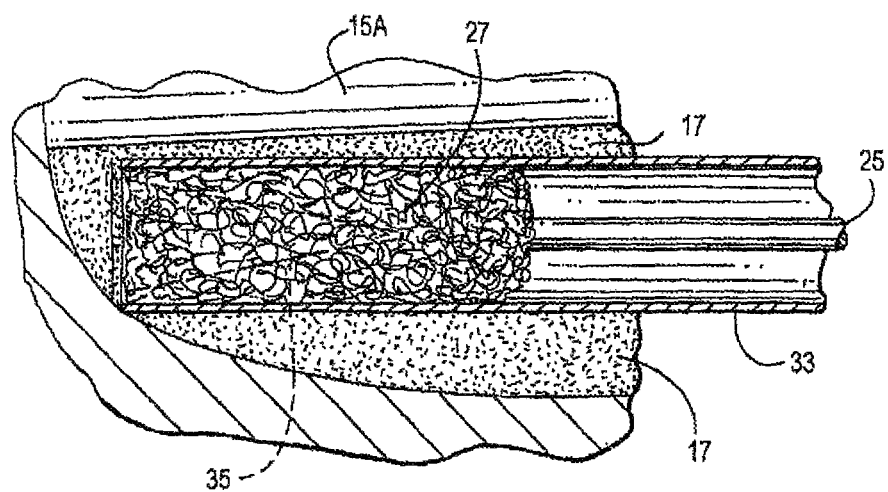
FIG. 9 is a cross-sectional view taken along line 9-9 of FIG. 8.

As shown in FIG. 4, an ingrown toenail condition is depicted in which a portion 26 of the nail fold 20 (see FIG. 2) is overgrown around a portion of the nail plate 15. As a result, the nail plate 15 penetrates flesh (i.e., the nail fold 20) surrounding the nail 13, causing an infection in the tissue region 28 (see FIG. 2) in which the nail plate 15 is buried.

As described hereinbefore and as illustrated in FIGS. 4 and 5, to address an in-grown nail condition, a P & A procedure is commonly carried out. Prior to the surgical procedure, the ingrown portion of nail plate 15 is first cut away or otherwise removed (see FIG. 3), leaving behind a remaining portion 15A of the nail plate 15 (see FIG. 5). During the P & A procedure, an applicator 25 that has an absorbable tip 27 is used to apply a phenol or similar solution to the surgical site. Known surgical applicators can be comprised of wood and have a cotton moisture absorbing tip affixed to one end. As shown in FIGS. 4 and 5, the tip 27 of the applicator 25 is inserted into a phenol or similar solution. As shown, for example, in FIG. 5, following removal of the ingrown portion of nail plate 15, the tip 27 of the applicator 25 is then inserted under the nail fold 20 so that the tip 27 can contact the nail matrix 21. By contacting the nail matrix 21, the portion of the nail matrix 21 that was producing the ingrown portion of the nail plate 15 can be ablated and thereby destroyed. However, the problem with carrying out this procedure, as previously described, is that the phenol or similar solution that is absorbed onto the tip 27 of the applicator 25 regularly contacts the skin and the nail bed 17, which causes burning and damage to those soft tissue areas, thereby slowing down the subsequent healing process.

FIG. 6 illustrates an embodiment of an applicator unit 31 that includes a tube 33 and an applicator 25 that is designed to reduce post-operative healing time, post-operative infection, and post-operative pain that, as described above, is commonly caused by known application devices. The tube 33 includes a body 34 with a first end 36 and a second end 38 and that has a channel 39 that extends therethrough to selectively receive the applicator 25 and a flap 35, or protrusion, at one end that aids in protecting the skin from phenol or a similar solution. In an embodiment, the tube 33 is comprised of a malleable material (e.g., plastic) and can be of any length and shape. In an embodiment, the tube 33 can be comprised of a plastic material that is resilient to acid, is flexible and can be autoclaved. In an embodiment, the tube 33 is substantially cylindrical. In an embodiment, the flap 35 is substantially rectangular. In an embodiment, the flap 35 is formed integral with and extends from the body 34 of the tube 33 at a first angle where the flap 35 extends toward the second end 38. In an embodiment, the flap 35 is formed integral with and extends from the tube 33 at a second angle that is opposite the first angle such that the flap extends away from the second end 38. The flap 35 is a flexible member that is preferably not a separate element from the tube 33, does not require a spring or a hinge and does not rotate.

In operation, the first end 36 of the tube 33 and the flap 35 are compressed upon an application of pressure from a first, resting state, to a second, compressed state. This is achieved by flap 35 contacting the body 34 of the tube 33 and the tube 33 is then flattened to allow the flap 35 and tube 33 to fit underneath the nail fold 20. Pressure is then released from the tube 33 and flap 35 to allow the tube 33 and flap 35 to expand toward an initial resting state and in turn lifting the nail fold 20 away from the nail matrix 21. The tip 27 of the applicator 25 is then placed in phenol or a similar solution, inserted into the second end 38 of the tube 33 and slid toward the first end 36 of the tube 33 to contact the nail matrix 21. The tube 33 and flap 35 thus aid in preventing phenol or similar solutions from contacting surrounding skin as well as the nail bed 17. This is accomplished by lifting the skin away from the nail matrix 21 so that contact of phenol or a similar solution is directed specifically toward the nail matrix 21 and contact with the skin is greatly reduced, if not substantially eliminated.

After applying the phenol or a similar solution carried by applicator tip 27 to nail matrix 21, alcohol is applied to nail bed 17 for irrigation purposes in order to remove the phenol or a similar solution and pressure is again applied to the flap 35 and the tube 33 to slide the tube 33 out from beneath the skin. The site of the procedure is preferably irrigated after the tube is removed.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention.

What is claimed is:

1. A method for treating an ingrown condition of a nail that is attached to a nail matrix, sits on a nail bed and is substantially surrounded by a nail fold at a base of the nail, the method comprising the steps of:
   providing a tube that includes a body having a first end, a second end and a flap extending from the body of the tube adjacent the first end of the tube at an angle;
   removing an ingrown part of a nail plate;
   determining a portion of the nail matrix from which the ingrown part of the nail plate has grown;
   applying pressure on the first end of the tube and the flap to compress the first end of the tube and orientate the flap such that the flap is substantially in contact with the body of the tube;
   disposing the tube and the flap underneath a nail fold;
   releasing the pressure from the first end of the tube and the flap such that the first end of the tube expands and the flap moves toward an initial resting position to contact the nail fold and maintain a separation of the nail fold from the nail matrix;
   applying a solution to a first end of an applicator;
   sliding the first end of the applicator into and through the second end of the tube;
   exposing the first end of the applicator through the first end of the tube; and
   contacting the nail matrix with the first end of the applicator to apply the solution onto substantially only the nail matrix, thereby ablating the nail matrix.

2. The method of claim 1, wherein the tube is comprised of a flexible material.

3. The method of claim 2, wherein the flexible material is one of a plastic, synthetic or an elastomeric material.

4. The method of claim 1, further comprising the step of irrigating the nail bed and the nail matrix to remove the solution applied thereto.

5. The method of claim 1, wherein the tube is cylindrical.

6. The method of claim 1, wherein the tube is transparent or opaque.

7. The method of claim 1, wherein the flap is substantially rectangular.

8. The method of claim 1, wherein the flap is disposed at a first angle extending toward the second end of the tube.

9. The method of claim 1, wherein the flap is disposed at a first angle extending toward the first end of the tube.

10. A method for treating an ingrown nail condition of a nail that is attached to a nail matrix, sits on a nail bed and is substantially surrounded by a nail fold at a base of the nail and along sides of the nail, the method comprising the steps of:
    removing an ingrown part of a nail plate;
    determining a portion of the nail matrix from which the ingrown part of the nail plate has grown;
    providing an application device that includes a hollow tube having a first end, a second end and a flap extending from the second end of the tube;
    applying pressure on the first end of a tube and the flap to compress the first end of the tube and orientate the flap such that the flap is substantially in contact with a body of the tube;
    disposing the tube and the flap underneath a nail fold;
    releasing the pressure from the first end of the tube and the flap such that the first end of the tube expands and the flap moves toward an initial resting position to contact the nail fold and maintain a separation of the nail fold from the nail matrix;
    applying a solution to a first end of an applicator;
    sliding the first end of the applicator into and through the second end of the tube;
    exposing the first end of said applicator through the first end of the tube; and
    contacting the nail matrix with the first end of the applicator to apply the solution substantially only on the nail matrix thereby ablating the nail matrix.

11. The method of claim 10, wherein the tube is comprised of a flexible material.

12. The method of claim 11, wherein the flexible material is one of a plastic, synthetic or an elastomeric material.

13. The method of claim 10, further comprising the step of compressing the first end of the tube after the solution is applied to the nail matrix and removing the tube from the nail matrix.

14. The method of claim 10, wherein the tube is cylindrical.

15. The method of claim 10, wherein the tube is transparent or opaque.

16. The method of claim 10, wherein the flap is substantially rectangular.

17. The method of claim 10, wherein the flap is disposed at an angle extending toward the second end of the tube.

18. The method of claim 10, wherein the flap is disposed at an angle extending toward the first end of the tube.

* * * * *